US006845265B2

(12) United States Patent
Thacker

(10) Patent No.: US 6,845,265 B2
(45) Date of Patent: Jan. 18, 2005

(54) SYSTEMS AND METHODS FOR LOCATING A TOOTH'S APICAL FORAMEN

(75) Inventor: Daniel Thacker, Snohomish, WA (US)

(73) Assignee: Aseptico, Inc., Woodinville, WA (US)

( * ) Notice: Subject to any disclaimer, the term of this patent is extended or adjusted under 35 U.S.C. 154(b) by 43 days.

(21) Appl. No.: 10/205,966

(22) Filed: Jul. 26, 2002

(65) Prior Publication Data

US 2004/0019291 A1 Jan. 29, 2004

(51) Int. Cl.[7] .............................. A61B 5/05; A61B 5/103
(52) U.S. Cl. ...................... 600/547; 600/590; 433/27; 33/513
(58) Field of Search ................................. 600/547, 590; 433/27, 28, 32, 72, 75, 215; 33/513, 514

(56) References Cited

U.S. PATENT DOCUMENTS

| | | | |
|---|---|---|---|
| 3,916,529 A | | 11/1975 | Mousseau |
| 3,993,044 A | | 11/1976 | McGuffin |
| 4,273,531 A | | 6/1981 | Hasegawa |
| 4,447,206 A | | 5/1984 | Ushiyama |
| 4,526,179 A | | 7/1985 | Salesky |
| 5,017,134 A | | 5/1991 | Saito et al. |
| 5,049,069 A | * | 9/1991 | Salesky ........................ 433/27 |
| 5,080,586 A | | 1/1992 | Kawai |
| 5,211,556 A | * | 5/1993 | Kobayashi et al. ............ 433/72 |
| 5,295,833 A | * | 3/1994 | Chihiro et al. ............... 433/224 |
| 5,759,159 A | | 6/1998 | Masreliez |
| 5,902,105 A | * | 5/1999 | Uejima et al. ................. 433/27 |
| 6,059,569 A | * | 5/2000 | Otsuka ......................... 433/72 |
| 6,425,875 B1 | * | 7/2002 | Reifman et al. ............. 600/590 |

* cited by examiner

*Primary Examiner*—Charles Marmor
(74) *Attorney, Agent, or Firm*—Graybeal Jackson Haley, LLP

(57) ABSTRACT

An apical foramen locator that a dental or medical practitioner can use to quickly and accurately identify the location of a patient's apical foramen during a dental/medical procedure is provided. The apical foramen locator determines the location of the apical foramen relative to a tool inserted into the patient's tooth by sensing an impedance—typically the voltage across two electrodes—and a stimulus voltage, and retrieving from an impedance map apical foramen location data that corresponds to the sensed impedance. The apical foramen locator can include a power circuit operable to apply a stimulus voltage across two electrodes and a reference resistor, an impedance-sensing circuit operable to read the stimulus voltage, a first voltage across the electrodes and a second voltage across the reference resistor and a processing component operable to derive first and second voltage indices from the stimulus, first and second voltages. Impedance maps can be generated using the apical foramen locator on reference teeth and can be stored in a memory used by the processing component.

25 Claims, 5 Drawing Sheets

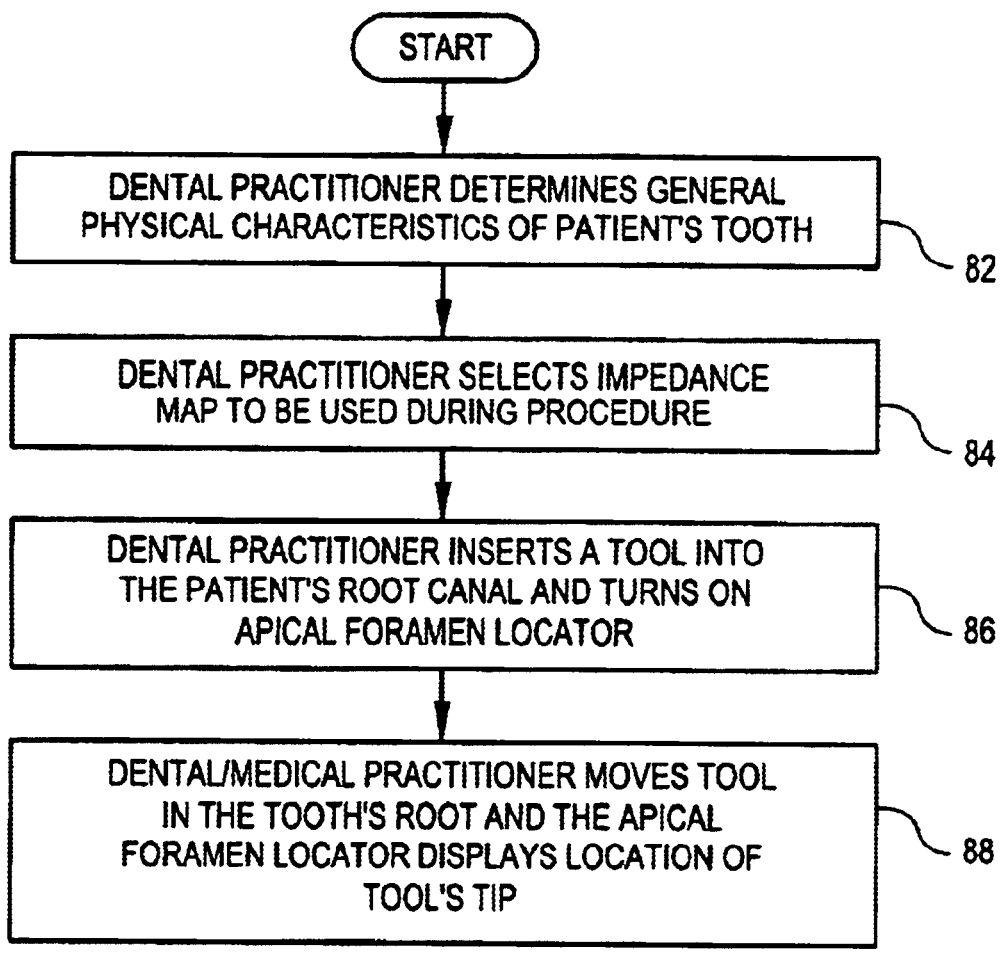

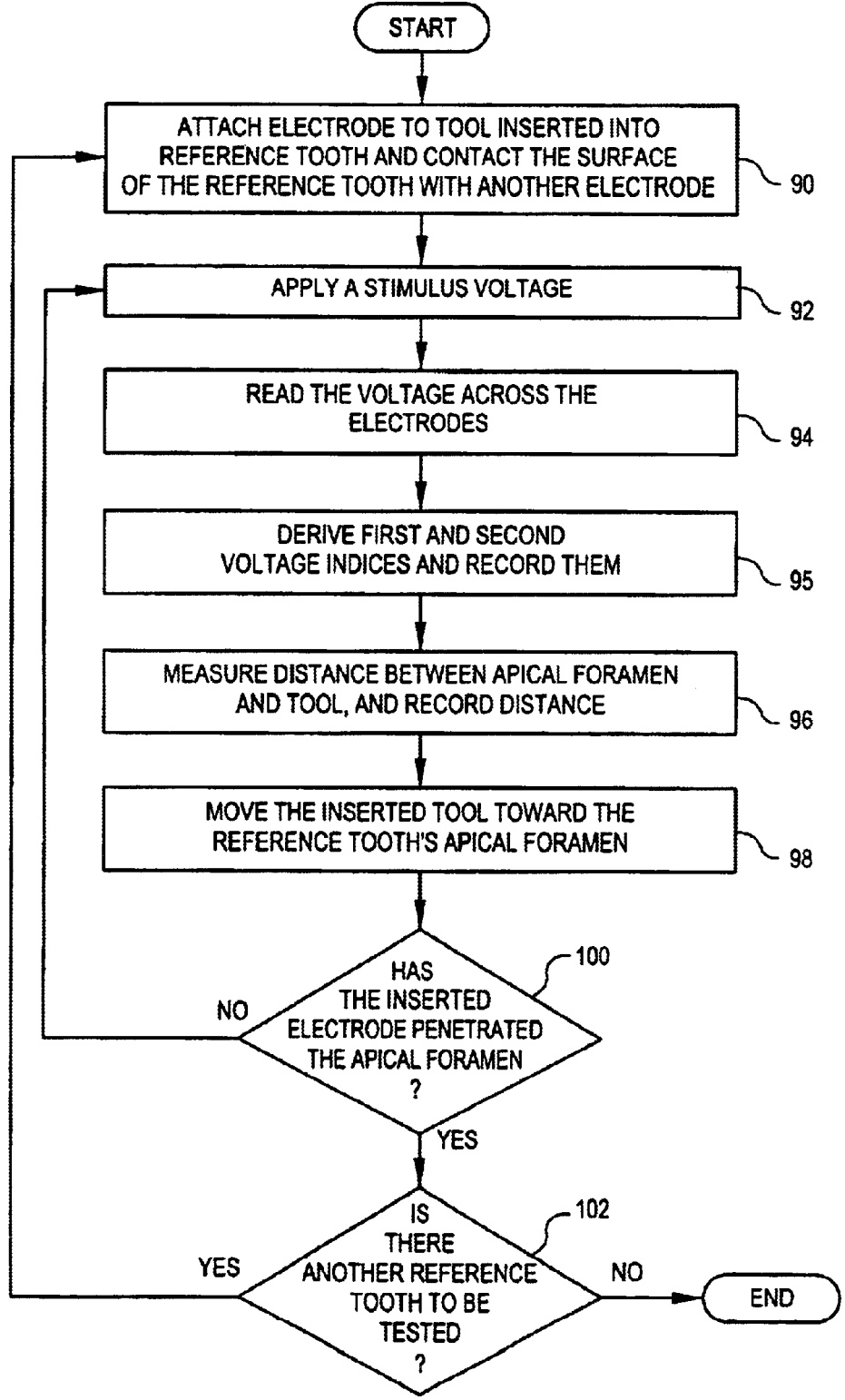

SYSTEMS AND METHODS FOR LOCATING A TOOTH'S APICAL FORAMEN

BACKGROUND

Many dental or medical procedures, such as cleaning a root canal, require the dental/medical practitioner to know the location of the apex of a patient's tooth. The apex is the location of the tooth's root where nerve, vascular and other tissue leave the jawbone and enter the tooth's root canal and is commonly referred to as the apical foramen. These dental/medical procedures typically involve inserting a file or other tool into the root canal of a patient's tooth to remove tissue from the canal. If the dental/medical practitioner does not insert the file or other tool to the apical foramen, nerve, vascular and other tissue can remain in the tooth's root canal. This remaining tissue can become infected and create more problems for the patient. If the dental/medical practitioner penetrates the apical foramen, healthy nerve, vascular and other tissue can be damaged. Such damage can cause unnecessary pain for the patient. Consequently, a number of methods and devices currently exist to help the dental/medical practitioner determine the location of the apical foramen of a specific tooth.

One such method and device includes taking numerous radiographs, such as x-rays with an x-ray machine, of a patient's tooth while the dental or medical practitioner moves a dental tool in the root canal. Unfortunately, this method has some drawbacks. This method subjects the patient to multiple exposures of radiation as the dental or medical practitioner moves the dental tool toward the apical foramen. This method can also be very time consuming because the dental or medical practitioner does not move the dental tool while the patient's tooth is radiographed and the radiographs developed. This method can also fail to show the location of the apical foramen relative to a dental tool if the tooth cannot be isolated on a radiograph.

Another such method and device includes electronically detecting the apical foramen's location by measuring changes in impedance between an electrode in a patient's tooth (often the tool) and an electrode attached to the patient's lip. Typically, a stimulus voltage applied across these electrodes includes two or more signals. One signal has a high frequency while the other signal has a lower frequency. By monitoring the changes in the impedance associated with each signal as the dental or medical practitioner moves the tool in the root canal, the dental or medical practitioner can obtain an approximate location of the tooth's apical foramen relative to the tool.

While this generally solves the problems associated with using radiographs, this method also has some drawbacks. Abnormal teeth, such as teeth with one or more lateral or accessory canals that also extend between a tooth's root canal and the surrounding jawbone, teeth with fillings, tooth decay and no apical constriction can cause negligible or unpredictable changes in impedance when the stimulus voltage is applied to the electrodes. Thus, such methods and devices can provide the dental or medical practitioner with significantly incorrect information about the location of the apical foramen relative to the tool. In addition, variations in each applied signal can cause an impedance response that incorrectly identifies the relative location of the apical foramen.

Thus, there is a need for an apical foramen locator that can quickly and accurately identify the location of a tooth's apical foramen.

SUMMARY

The present invention provides an apical foramen locator that a dental or medical practitioner can use to quickly and accurately identify the location of a tooth's apical foramen during a dental/medical procedure. The apical foramen locator determines the location of the apical foramen relative to a tool inserted into the patient's tooth by sensing an impedance to a stimulus voltage and retrieving from an impedance map apical foramen location data that corresponds to the sensed impedance. The stimulus voltage can have a single frequency. Thus, the accuracy of the apical foramen locator is not adversely affected by variations in the multiple frequencies of the stimulus voltage used in conventional locators. The apical foramen location data in the impedance map is derived from reference teeth. And, the apical foramen locator can include more than one impedance map appropriate for different tooth geometries, such as a curved root or specific ranges of cementum thicknesses, or different tooth abnormalities, such as one or more lateral or accessory canals, one or more fillings, tooth decay, or lack of an apical constriction. Thus, the accuracy of the apical foramen locator can be enhanced for different tooth geometries or tooth abnormalities.

In one aspect of the invention the apical foramen locator can include a power circuit to apply a stimulus voltage across two electrodes and a reference resistor, wherein the reference resistor is connected to one of the electrodes. The apical foramen locator can also include an impedance-sensing circuit operable to read the stimulus voltage, a first voltage across the electrodes and a second voltage across the reference resistor. The apical foramen locator can also include a processing component operable to derive first and second voltage indices from the applied stimulus voltage and the sensed first and second voltages. To determine the relative location of the apical foramen, the processing component selects from the impedance map apical foramen location data that corresponds to the derived first and second voltage indices.

In another aspect of the invention, impedance maps can be generated using the apical foramen locator on reference teeth. The impedance maps are generated by recording distances between the tool and the apical foramen of a reference tooth, and recording the voltage indices associated with the tool at each distance. From these recordings, apical foramen location data are generated. The reference teeth can include normal teeth or abnormal teeth, and the number of teeth used to generate an impedance map can include a few or many. For example, the reference teeth used to generate an impedance map for normal molars can include a few normal molars. And the reference teeth used to generate an impedance map for abnormal cuspids, bicuspids and incisors can include many cuspids, bicuspids and incisors having fillings or can include many cuspids, bicuspids and incisors having accessory canals or many cuspids, bicuspids and incisors having any other desired type of abnormality. Other impedance maps can be generated from reference teeth subject to different conditions during the dental/medical procedure, such as a wet canal (a significant amount of a tooth's pulp in the tooth's canal), dry canal (a significant amount of a tooth's pulp not present in the tooth's canal), or any desired fluid in the tooth's canal. Thus, many different impedance maps corresponding to different tooth abnormalities can be generated. Consequently, the apical foramen locator can accurately provide the location of the apical foramen of abnormal teeth.

In another aspect of the invention, a method for using the apical foramen locator to locate a patient's apical foramen during a dental/medical procedure, and a method for generating an impedance map are provided. A method for locating a patient's apical foramen can include a) applying a stimulus voltage across two electrodes and a reference resistor, wherein one electrode contacts a tool inserted into the root canal of a patient and the other electrode contacts another region of the patient; b) sensing the stimulus voltage, a first voltage across the two electrodes and a second voltage across a reference resistor; c) deriving a first voltage index and a second voltage index from the stimulus, first and second voltages and d) selecting from an impedance map apical foramen location data that corresponds to the combination of the first and second voltage indices.

In another aspect, a method for generating an impedance map can include a) applying a voltage across two electrodes and a reference resistor, wherein one electrode contacts a tool inserted into the root canal of a reference tooth and the other electrode contacts a surface of the same reference tooth; b) sensing the voltage across the two electrodes and reference resistor, c) recording voltage indices derived from the applied voltage and the sensed voltages; d) recording the distance between the tool inserted into the root canal and the tooth's apical foramen; d) moving the inserted tool toward the reference tooth's apical foramen; e) repeating the foregoing.

BRIEF DESCRIPTION OF THE FIGURES

FIG. 5 is a flow chart of a process for using the apical foramen locator in FIG. 1 to determine the location of a patient's apical foramen during a dental/medical procedure, according to an embodiment of the invention.

FIG. 6 is a flow chart of a process for generating an impedance map from reference teeth, according to an embodiment of the invention.

DETAILED DESCRIPTION

Figure 1:
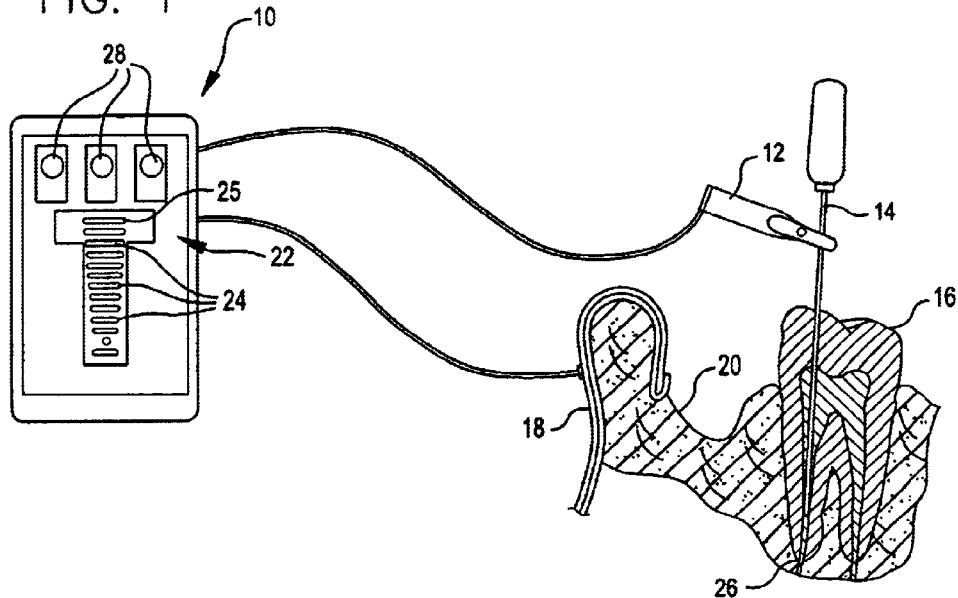
FIG. 1 is a perspective view of an apical foramen locator according to an embodiment of the invention with an electrode attached to a tool in the patient's tooth and another electrode attached to the patient's lip.

The present invention provides an apical foramen locator that a dental or medical practitioner can use to quickly and accurately identify the location of a patient's apical foramen during a dental/medical procedure. The apical foramen locator determines the location of the apical foramen relative to a tool inserted into the patient's tooth by sensing an impedance—typically the voltage across two, electrodes—and a stimulus voltage, and retrieving from an impedance map apical foramen location data that corresponds to the sensed impedance. By using an impedance map generated from reference teeth similar to the patient's tooth and a stimulus voltage having a single frequency, the apical foramen locator can quickly and accurately identify the location of a tooth's apical foramen.

The apical foramen locator can include a power circuit operable to apply a stimulus voltage across two electrodes and a reference resistor, wherein the reference resistor is connected to one of the electrodes. The apical foramen locator can also include an impedance-sensing circuit operable to read the stimulus voltage, a first voltage across the electrodes and a second voltage across the reference resistor. The apical foramen locator can also include a processing component operable to derive first and second voltage indices from the stimulus, first and second voltages. To determine the relative location of the apical foramen, the processing component selects from the impedance map apical foramen location data that corresponds to the derived first and second voltage indices.

Impedance maps can be generated using the apical foramen locator on reference teeth and can be stored in a memory of the processing component. The impedance maps are generated by recording distances between the tool and the apical foramen of a reference tooth, and recording the voltage indices (hence the impedances) associated with the tool at each distance. From these recordings, apical foramen location data are generated. The reference teeth can include normal or abnormal teeth, such as teeth with one or more lateral or accessory canals that also extend between a tooth's root canal and the surrounding jawbone, teeth with fillings, tooth decay, or no apical constriction. In addition, a few or many reference teeth can be used to generate an impedance map. Thus, many different impedance maps corresponding to different tooth abnormalities can be generated. Consequently, the apical foramen locator can quickly and accurately determine the location of the apical foramen of abnormal and normal teeth.

The scope of the present invention includes both means plus function and step plus function concepts. However, the terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

All terms used herein, including those specifically described below in this section, are used in accordance with their ordinary meaning unless the context or definition indicates otherwise. Also unless indicated otherwise, except within the claims, the use of "or" includes "and" and vice-versa. Non-limiting terms are not to be construed as limiting unless expressly stated (for example, "including" and "comprising" mean "including without limitation" unless expressly stated otherwise).

FIG. 1 is a perspective view of an apical foramen locator 10 according to an embodiment of the invention with an electrode 12 attached to a file 14 in the patient's tooth 16 and another electrode 18 attached to the patient's lip 20. In this and certain other embodiments, the locator 10 includes electronic circuits and components (not shown but discussed in greater detail elsewhere herein) for applying a stimulus voltage across the electrodes 12 and 18, sensing the impedance between the electrodes 12 and 18, and selecting apical foramen location data from an impedance map (not shown but discussed in greater detail elsewhere herein) stored in the locator 10. The locator 10 also includes a display 22 for presenting selected apical foramen location data to a dental or medical practitioner.

The display 22 can be any desired display capable of presenting apical foramen location data to the dental or medical practitioner. For example, in this and certain other embodiments, the display 22 can include lights 24 and 25 that can operate in a single mode, persistent mode, or a logarithmic march mode. In the single mode, an end light 25 can represent the point where the file 14 is at the tooth's apical foramen 26 or substantially close to the tooth's apical foramen 26. The other lights 24 can indicate the distance between the tip of the file 14 and the apical foramen 26 by their proximity to the end light 25. Thus, as the tip of the file 14 approaches the tooth's apical foramen 26, single lights 24 are turned "on" and then "off" and appear to march toward the end light 24. In the persistent mode, the lights 24 and 25 can indicate the distance of the tip of the file 14 to the apical foramen 26 in a similar manner to the single light mode except the lights are not turned "off" after the tip of the tool 14 continues toward the apical foramen 26. In the logarithmic march mode, the number of lights 24 and 25 turned "on" can indicate the distance between the tip of the tool 14 and the apical foramen 26.

Still referring to FIG. 1, in other embodiments, the lights of the display can be color-coded as desired to provide the dental or medical practitioner an easily recognizable indication of the apical foramen's location. Additionally or alternatively, the display can include any desired sound to indicate the distance between the Up of the tool 14 and the apical foramen 26. For example, the display can provide beeps that can indicate the distance between the tip of the tool 14 and the apical foramen 26 based on the tone of the beep, the number of beeps or time between multiple beeps. In still other embodiments, the display can be a backlit liquid crystal display that presents text to the dental or medical practitioner or the display can be a video display that presents images to the dental or medical practitioner.

Still referring to FIG. 1, in this and certain other embodiments, the apical foramen locator 10 can include mode buttons 28 for selecting an impedance map appropriate for the patient's tooth and for changing how the apical foramen location data is displayed to the dental or medical practitioner. Thus, a dental or medical practitioner can quickly change impedance maps as desired. In addition, the dental or medical practitioner can receive the apical foramen location data in a manner that he/she is most comfortable with.

Figure 2:
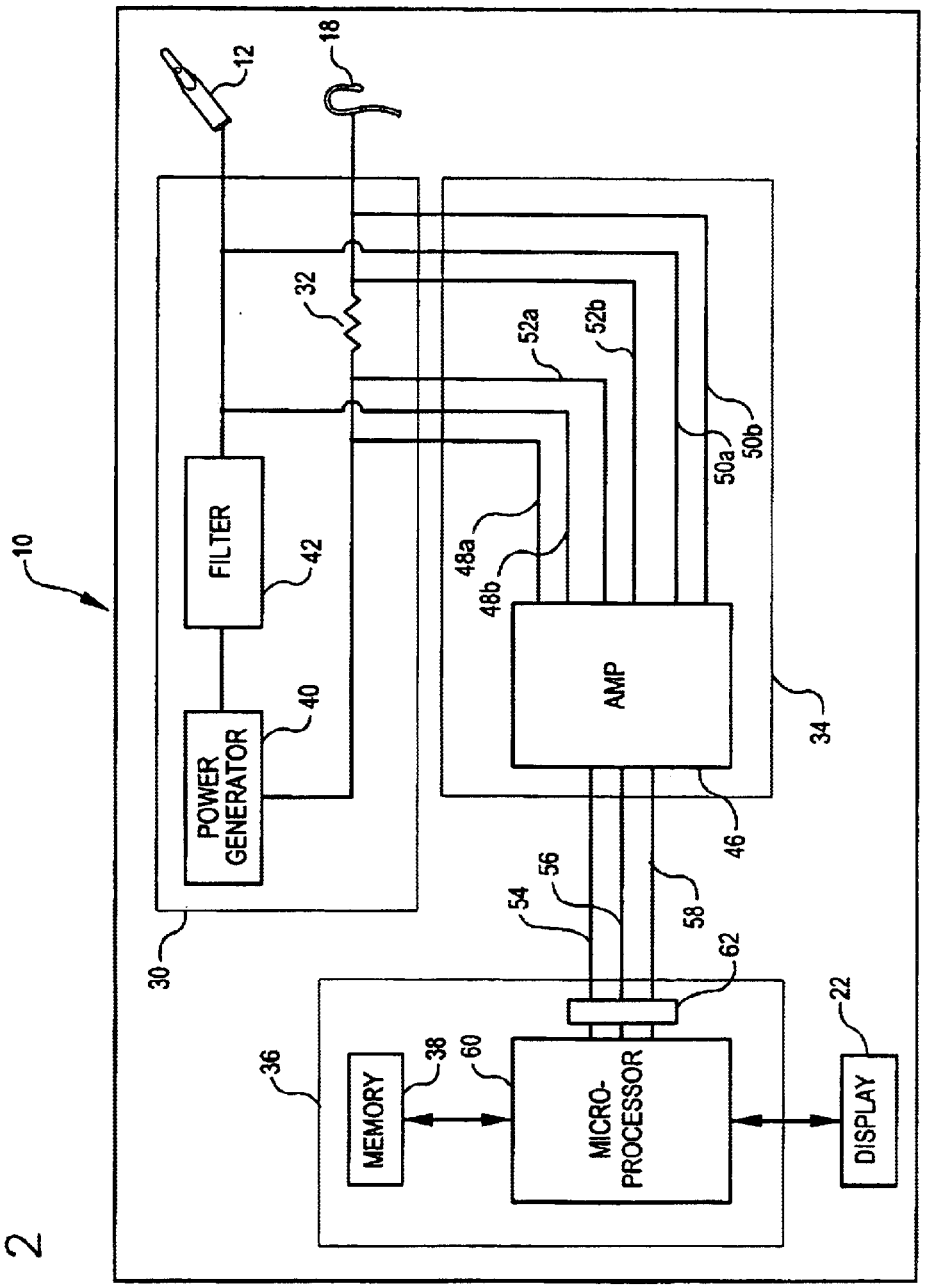
FIG. 2 is a schematic diagram of the apical foramen locator in FIG. 1, according to an embodiment of the invention.

FIG. 2 is a schematic diagram of electrical components and circuits included in the apical foramen locator 10 in FIG. 1, according to an embodiment of the invention. In this and certain other embodiments, the locator 10 includes a power circuit 30 for applying a stimulus voltage across the electrodes 12 and 18 and a reference resistor 32. The locator 10 also includes an impedance-sensing circuit 34 for sensing the voltage across the electrodes 12 and 18, sensing the voltage across the reference resistor 32 and sensing the stimulus voltage. The locator 10 also includes a processing component 36 for deriving first and second voltage indices and selecting apical foramen location data from an impedance map stored in a memory 38 of the processing component 36.

In this and certain other embodiments, the power component 30 can include a power generator 40 for generating a stimulus voltage and a filter 42 for removing undesired voltage amplitudes in the stimulus voltage, thus changing the waveform of the stimulus voltage. The power generator 40 can be any conventional power generator capable of producing a voltage having any desired frequency and wave form such as a sine wave or a square wave. The filter 42 can be any conventional filter capable of isolating the desired stimulus voltage and waveform. For example, in this and certain other embodiments, the power generator 40 can produce a five volt peak-to-peak square wave with a frequency of 30 kilohertz (kHz) and the filter 42 can be a low-pass filter that can produce a 100 millivolt (mV) peak-to-peak sine wave with the same frequency.

By using a stimulus voltage having a single frequency, the apical foramen locator 10 can provide more accurate information about the location of a tooth's apical foramen relative to the tip of the tool 14. Power generators typically produce a voltage whose frequency includes minor variations. For example, a voltage having a frequency of 30 kHz can have a frequency between 30.01 kHz and 29.99 kHz. Because the apical foramen locator 10 and conventional locators sense the impedance, which includes some capacitance, between two electrodes to determine the position of a tooth's apical foramen, variations in the stimulus voltage's frequency can affect the accuracy of these locators. Consequently, the accuracy of locators that use a stimulus voltage having two or more frequencies can be subject to minor variations in either or all of the frequencies. Thus, the fewer the number of frequencies included in the stimulus voltage, the more accurate the apical foramen can become. Consequently, by using a stimulus voltage having a single frequency, the apical foramen locator 10 can be more accurate than conventional locators that use multiple frequencies.

Still referring to FIG. 2, in other embodiments, the filter 42 can be adjustable to provide any desired modification of the stimulus voltage generated by the power generator 40. Additionally or alternatively, the power generator 40 can be adjustable to provide any desired voltage with any desired waveform at any desired frequency.

Still referring to FIG. 2, the reference resistor 32 can be any desired conventional resistor. For example, in this and certain other embodiments, the resistor 32 can be a 2,320 Ohm resistor. Additionally or alternatively, the reference resistor 32 can be adjustable to provide any desired resistance. This may also be desirable when different impedance maps are generated using apical foramen locators having reference resistors with different resistance values.

Still referring to FIG. 2, in this and certain other embodiments, the impedance-sensing circuit 34 can include an amplifier 46 and leads 48a and 48b for sensing the stimulus voltage, leads 50a and 50b for sensing a first voltage or the voltage across the electrodes 12 and 18, and leads 52a and 52b for sensing a second voltage or voltage across the reference resistor 32. The amplifier 46 can read the stimulus, first and second voltages, and can amplify these voltages for the processing component 36. Leads 54, 56 and 58 can then convey the amplified stimulus, first and second voltages, respectively, to the processing component 36.

Still referring to FIG. 2, in this and certain other embodiments, the processing component 36 can include a microprocessor 60 and memory 38 for performing functions such as executing software to perform tasks. The processing component 36 can also include an analogue-to-digital converter 62 for converting the stimulus, first and second voltages from the amplifier 46 into digital data that the microprocessor 60 can use. From the digital data, the microprocessor 60 can derive a first voltage index and a second voltage index. The microprocessor 60 can use these first and second voltage indices to select apical foramen location data from an impedance map stored in the memory 38.

Still referring to FIG. 2, the first and second voltage indices can be derived in any desired manner as long as the derivation of the first and second voltage indices by the microprocessor 60 is consistent with the derivation of the indices of the desired impedance map. For example, in this and certain other embodiments, the first and second voltage indices are derived from ratios of the stimulus, first and second voltages to the other voltages.

Still referring to FIG. 2, in this and certain other embodiments, the memory 38 can be fixed to the processing component 36, removably attachable to the processing component 36, or can include a portion that is fixed and another portion that is removably attachable to the processing component 36. For example, the memory 38 can include any desired removable storage media such as a floppy disc, compact disc, magnetic tape or removable hard drive that can store an impedance map and instructions for the microprocessor 60.

Still referring to FIG. 2, in operation, a dental or medical practitioner inserts the tool 14 (FIG. 1) into the root canal of a patient's tooth, attaches the electrode 12 to the tool 14 and attaches the electrode 18 to the patients lip 20 (FIG. 1). The dental or medical practitioner then turns "on" the apical foramen locator 10. Alternatively, the dental or medical practitioner can first turn "on" the apical foramen locator 10 and then attach the electrodes 12 and 18. In operation, the power circuit 30 generates a stimulus voltage having a single frequency across the electrodes 12 and 18 and the reference resistor 32. The amplifier 46 of the impedance-sensing component senses the first voltage across the electrodes 12 and 18, senses the second voltage across the reference resistor 32 and senses the stimulus voltage. The amplifier 46 then amplifies these voltages. The analogue-to-digital converter 62 of the processing component 36 receives these voltages and converts them into digital data. The microprocessor 60 receives the digital data and derives first and second voltage indices from this data. After deriving the indices, the microprocessor 60 selects apical foramen location data from an impedance map that corresponds to the derived indices. The microprocessor 60 then instructs the display 22 to present the apical foramen location data. This process is continuously repeated as the dental or medical practitioner moves the tool 14 toward the tooth's apical foramen 26 (FIG. 1).

Figure 3:
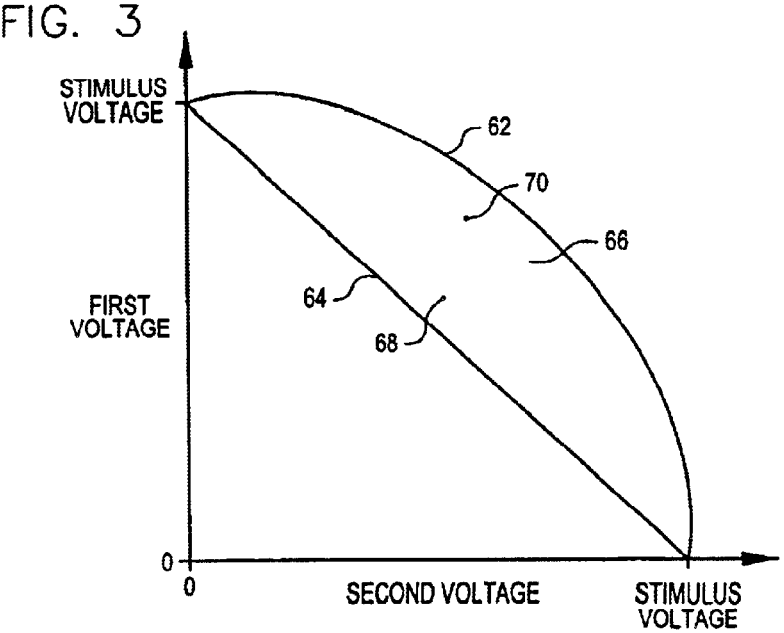
FIG. 3 is a graph showing a range of possible voltages the apical foramen locator in FIG. 1 can sense.
Figure 4:
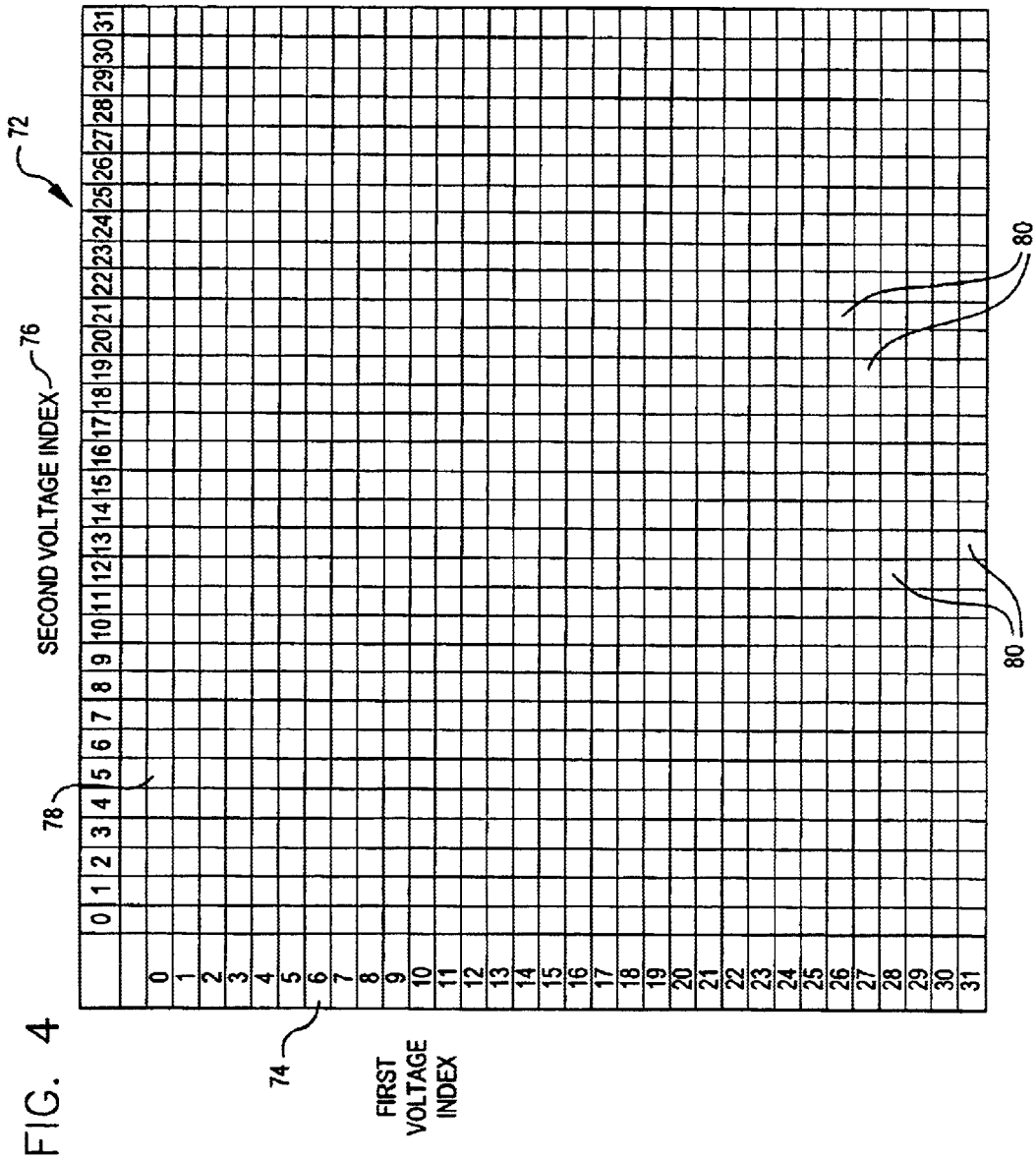
FIG. 4 is an impedance map generated from reference teeth that includes a table of apical foramen location data, according to an embodiment of the invention.

FIG. 3 is a graph showing a range of possible first voltages across the electrodes 12 and 18 (FIGS. 1 and 2) and possible second voltages across the reference resistor 32 (FIG. 2) that can be sensed by the impedance-sensing circuit 34 (FIG. 2). FIG. 4 is an impedance map generated from reference teeth that includes a table of apical foramen location data, according to an embodiment of the invention.

Referring to FIG. 3, when the electrodes 12 and 18 are attached to a patient as discussed elsewhere herein, the impedance between the electrodes 12 and 18 typically includes a resistive element and a capacitive element. The line 62 represents the first and second voltages that the impedance-sensing circuit 34 would sense if the impedance between the electrodes 12 and 18 only included a capacitive element. The line 64 represents the first and second voltages that the impedance-sensing circuit 34 would sense if the impedance between the electrodes 12 and 18 only included a resistive element. The location on the graph where the second voltage is zero and the first voltage equals the stimulus voltage, the lines 62 and 64 intersect and is analogous to an open circuit between electrodes 12 and 18. The location on the graph where the first voltage is zero and the second voltage equals the stimulus voltage, the lines 62 and 64 intersect and is analogous to a short across the electrodes 12 and 18. Consequently, the region 66 defined by the area between the lines 62 and 64 represents the possible first and second voltages sensed by the impedance-sensing circuit 34.

Still referring to FIG. 3, as a dental or medical practitioner moves the file 14 (FIGS. 1 and 2) toward or away from the apical foramen of a tooth, the impedance, as represented by the first and second voltages, sensed by the impedance-sensing circuit can be plotted in the region 66. For example, when the file 14 is initially inserted into a tooth, the impedance-sensing component 34 may sense a first voltage that is approximately one half of the stimulus voltage and a second voltage that is slightly greater than the first voltage (indicated by the point 68). Then, when the file 14 is closer to the tooth's apical foramen, the impedance-sensing component 34 may sense a first voltage that is greater than one half of the stimulus voltage and a second voltage that is also greater than one half of the stimulus voltage (indicated by the point 70).

Thus, an association between the location of the tip of the file 14 relative to the apical foramen of a tooth, and the first and second voltages sensed by the impedance-sensing circuit 34 can be plotted to generate an impedance map. And in turn, this association and an impedance map can be used to determine the location of the apical foramen in a patient's tooth relative to the tip of a tool during a procedure.

Referring to FIG. 4, in this and certain other embodiments, an impedance map 72 is generated from reference teeth and includes a first voltage index 74, a second voltage index 76 and apical foramen location data 78. The impedance map 72 corresponds each combination of the first and second voltage indices 74 and 76 with specific apical foramen location data 80. Thus, during a dental/medical procedure, apical foramen location data 80 is retrieved by the microprocessor 60 (FIG. 2) based on the first and second voltage indices derived during the procedure, and provides the dental or medical practitioner an indication of the tool tip's location relative to the patient's apical foramen.

The reference teeth used to generate the impedance map 72 can include teeth that have a similar physical geometry, such as a curved root or specific ranges of cementum thicknesses, or a similar abnormality, such as one or more lateral or accessory canals, fillings, tooth decay, or lack of an apical constriction. In addition, the number of reference teeth used can be any number desired. For example, the reference teeth used to generate an impedance map for normal molars can include a few molars that have a substantially straight root. Likewise, the reference teeth used to generate an impedance map for abnormal cuspids, bicuspids, or incisors can include many cuspids, bicuspids, or incisors having fillings or can include many cuspids, bicuspids, or incisors having lateral accessory canals or many cuspids, bicuspids, or incisors having any other desired type of abnormality. Other impedance maps can include reference teeth subject to different conditions during a dental/medical procedure, such as a wet canal (a significant amount of a tooth's pulp in the tooth's canal), dry canal (a significant amount of a tooth's pulp not present in the tooth's canal), or any desired fluid in the tooth's canal. Thus, many different impedance maps corresponding to different tooth abnormalities can be generated. Consequently, the apical foramen locator can accurately provide the location of the apical foramen of teeth having different geometries or abnormalities.

Still referring to FIG. 4, to generate the apical foramen location data 78, and first and second voltage indices 74 and 76, the apical foramen locator 10 (FIGS. 1 and 2) senses the impedance of each reference tooth as the file 14 (FIGS. 1 and 2) is moved toward or away from the reference tooth's apical foramen. These sensed impedances and the distance of the file 14 relative to the reference tooth's apical foramen when the impedance was sensed are recorded. From these recordings, the apical foramen location data 78, and first and second voltage indices 74 and 76 are generated. Thus, during a dental/medical procedure, the first and the second voltage indices derived by the microprocessor 60 (FIG. 2,) is matched with a first and a second voltage index in the impedance map, and the corresponding apical foramen location data provides the location of the file 14 relative to the patient's apical foramen.

FIG. 5 is a flow chart of a process for using the apical foramen locator in FIG. 1 to determine the location of a patient's apical foramen during a dental or medical procedure, according to an embodiment of the invention.

In this and certain other embodiments, at step 82, a dental or medical practitioner first determines the physical geometry of the patient's tooth and whether any tooth abnormalities exist. The dental or medical practitioner can determine these by taking a radiograph of the patient's tooth or by visually inspecting the tooth or by any desired method. Next, at step 84, the dental or medical practitioner can select an appropriate impedance map 72 (FIG. 4). As discussed elsewhere herein, the appropriate impedance map 72 can already be stored in the memory 38 (FIG. 2) of the processing component 36 (FIG. 2) or the appropriate impedance map 72 can be loaded into the memory 38 of the processing component 36. Then, at step 86, the dental or medical practitioner can insert a file 14 (FIGS. 1 and 2) into the root of the patient's tooth, can attach an electrode 12 (FIGS. 1 and 2) to the file 14 and an electrode 18 to the patient's lip 20 (FIG. 1) and can turn "on" the apical foramen locator 10 (FIGS. 1 and 2). Then, at step 88, the dental or medical practitioner can move the file 14, and the apical foramen locator 10 can display the tool tip's location relative to the tooth's apical foramen.

FIG. 6 is a flow chart of a process for generating an impedance map from reference teeth, according to an embodiment of the invention.

In this and certain other embodiments, at step 90, an electrode of the apical foramen locator 10 (FIGS. 1 and 2) can be inserted into the root of a reference tooth and another electrode of the apical foramen locator 10 can be placed in electrical contact with the surface of the reference tooth. In other embodiments, the electrode can be inserted into the root of a reference tooth and the other electrode can be placed in electrical contact with a lip model that mimics the impedance of the tissue around the outside surface of a patient's tooth. Then, at step 92, the apical foramen locator 10 can apply a stimulus voltage across the electrodes and across the reference resistor 32 (FIG. 2). Then, at step 94, the apical foramen locator 10 can sense a first voltage across the electrodes and a second voltage across the reference resistor 32. At step 95, first and second voltage indices can be derived from the stimulus, first and second voltages. At step 96, the distance between the electrode and the reference tooth's apical foramen can be measured. This distance and the first and second voltage indices derived at this distance can then be recorded. Then, at step 98, the electrode inserted into the reference tooth can be moved toward the tooth's apical foramen. At step 100, if this electrode has not protruded through the reference tooth's apical foramen, then steps 92 through 98 can be repeated. If, however, the electrode does protrude through the apical foramen, then the electrode can be removed from the reference tooth. At step 102, if additional reference teeth remain to be used then steps 90 through 100 can be repeated.

Although systems and methods for locating a tooth's apical foramen have been described in considerable detail with reference to certain embodiments for purposes of illustration, other embodiments are possible. Therefore the spirit and scope of the appended claims should not be limited to the above description of the embodiments; the present inventions include suitable modifications as well as all permutations and combinations of the subject matter set forth herein.

What is claimed is:

1. An apical foramen locator comprising:
   a power circuit operable to generate a stimulus voltage across two electrodes and across a reference resistor connected to one of the electrodes;
   an impedance-sensing circuit operable to sense the stimulus voltage, a first voltage across the two electrodes and a second voltage across the reference resistor;
   at least one impedance map including apical foramen location data corresponding to a combination of a first voltage index and a second voltage index wherein the apical foramen location data is generated from reference teeth;
   a processing component including a memory storing the at least one impedance map and a microprocessor that is operable to derive the first and second voltage indices from the voltages sensed by the impedance-sensing circuit and to select from the impedance map apical foramen location data that corresponds to the first and second voltage indices; and
   a display operable to present the selected apical foramen location data.

2. The locator of claim 1 wherein the stimulus voltage has a single frequency.

3. The locator of claim 1 wherein the stimulus voltage includes a voltage having a waveform and a frequency.

4. The locator of claim 1 wherein the power circuit includes a filter operable to modify the stimulus voltage before the impedance-sensing circuit senses the stimulus voltage.

5. The locator of claim 4 wherein the filter is operable to modify the stimulus voltage to include a 100 mV peak-to-peak sine wave at 30 KHz.

6. The locator of claim 1 wherein one of the electrodes includes a lip clip and the other electrode is connected to a file.

7. The locator of claim 1 wherein the impedance sensing circuit includes an amplifier operable to amplify at least one of the following voltages: the stimulus voltage, the first voltage and the second voltage.

8. The locator of claim 1 wherein the processing component includes an analogue-to-digital converter operable to generate digital data from each of the respective stimulus, first and second voltages.

9. The locator of claim 1 wherein the apical foramen location data represents the location of a tip of a tool relative to a patient's apical foramen.

10. The locator of claim 1 wherein:
    the first voltage index is derived from the stimulus voltage and the first voltage; and
    the second voltage index is derived from the stimulus voltage and the second voltage.

11. The locator of claim 10 wherein:
    the first voltage index includes a ratio of the stimulus voltage to the first voltage and the second voltage index includes a ratio of the stimulus voltage to the second voltage.

12. The locator of claim 1 wherein:

one of the electrodes is connected to a tool adapted to be inserted into a root canal of a patient's tooth; and the display includes at least one of the following:

a visual display operable to indicate the location of a tip of the tool relative to the patient's apical foramen; and an aural display that includes sounds and is operable to indicate the location of a tip of the tool relative to the patient's apical foramen.

13. The locator of claim 1 further comprising a mode button operable to select an impedance map that the processing component uses to select apical foramen location data.

14. A method for locating an apical foramen of a patient's tooth, comprising:

applying a stimulus voltage across two electrodes and a reference resistor, wherein one electrode contacts a tool inserted into the root canal of the patient and the other electrode contacts another region of the patient;

sensing the stimulus voltage, a first voltage across the two electrodes and a second voltage across the reference resistor; and deriving a first and second voltage index from the stimulus, first and second voltages; and selecting from an impedance map apical foramen location data that corresponds to the combination of the first and second voltage indices.

15. The method of claim 14 wherein another region of the patient includes the lip of the patient.

16. The method of claim 14 wherein:

deriving the first voltage index includes deriving a ratio between the stimulus and first voltages; and deriving the second voltage index includes deriving a ratio between the stimulus and second voltages.

17. The method of claim 14 further comprising displaying the selected apical foramen location data.

18. The method of claim 17 wherein displaying the selected apical foramen data includes at least one of the following:

presenting at least one of the following: text and images; turning on a light; and providing a sound.

19. The method of claim 14 further comprising:

moving the tool toward the apical foramen of the patient's tooth; and reading the stimulus voltage, the first voltage and the second voltage as the tool is moved.

20. The method of claim 14 further comprising selecting an impedance map.

21. The method of claim 14 further comprising selecting an impedance map generated by reference teeth having at least one of the following, the same or substantially the same physical geometry as the patient's tooth and the same or substantially the same abnormality as the patient's tooth.

22. The method of claim 21 wherein selecting an impedance map includes comparing at least one of the following characteristics of a patient's tooth, physical geometry and abnormality, to a respective characteristic of the reference teeth used to generate the impedance map.

23. The method of claim 14 further comprising:

inserting a tool into a root canal of the patient's tooth; and contacting the tool with an electrode.

24. A method for generating an impedance map from reference teeth for use with an apical foramen locator, comprising:

a) applying a voltage across two electrodes and a reference resistor, wherein one electrode contacts a tool inserted into the root canal of one of the reference teeth and the other electrode contacts a surface of the same reference tooth;

b) sensing the voltage across the two electrodes and the reference resistor;

c) recording voltage indices derived from the applied voltage and the sensed voltages;

d) recording the distance between the tool inserted into the root canal and the tooth's apical foramen;

e) moving the inserted tool toward the reference tooth's apical foramen; and f) repeating a) through d).

25. The method of claim 24 further comprising repeating a) through f) using another one of the reference teeth.

* * * * *